(12) United States Patent
Choi et al.

(10) Patent No.: US 11,708,549 B2
(45) Date of Patent: Jul. 25, 2023

(54) BACTERIAL, FUNGAL, AND YEAST GROWTH INHIBITOR CONTAINING ALLULOSE

(71) Applicant: CJ CHEILJEDANG CORPORATION, Seoul (KR)

(72) Inventors: Jong Min Choi, Suwon-si (KR); Su-Jeong Kim, Suwon-si (KR); Youn-Kyung Bak, Suwon-si (KR); Jung Gyu Park, Incheon (KR); Sung Bae Byun, Sejong (KR); Dong Seok Shim, Yongin-si (KR); In Lee, Suwon-si (KR); Seung Won Park, Yongin-si (KR); Dong Chul Jung, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 687 days.

(21) Appl. No.: 16/328,825

(22) PCT Filed: Sep. 28, 2017

(86) PCT No.: PCT/KR2017/010821
§ 371 (c)(1),
(2) Date: Feb. 27, 2019

(87) PCT Pub. No.: WO2018/066890
PCT Pub. Date: Apr. 12, 2018

(65) Prior Publication Data
US 2020/0255778 A1    Aug. 13, 2020

(30) Foreign Application Priority Data
Oct. 6, 2016 (KR) .......................... 10-2016-0128949

(51) Int. Cl.
*C12G 3/022* (2019.01)
*C12H 1/14* (2006.01)
(Continued)

(52) U.S. Cl.
CPC ............... *C12G 3/022* (2019.02); *C12H 1/14* (2013.01); *C12G 2200/21* (2013.01); *C12N 1/16* (2013.01); *C12N 1/20* (2013.01)

(58) Field of Classification Search
CPC ........... C12N 1/16; C12N 1/20; A23L 3/3481; C12G 3/02; C12G 3/022; C12G 2200/21;
(Continued)

(56) References Cited

U.S. PATENT DOCUMENTS

| 8,017,828 B2 | 9/2011 | Izumori |
| 2008/0102161 A1 | 5/2008 | Ota et al. |

(Continued)

FOREIGN PATENT DOCUMENTS

| CA | 2931320 A1 | 5/2015 |
| CN | 101177672 A | 5/2008 |

(Continued)

OTHER PUBLICATIONS

JP-2010119335 (machine translation) (Year: 2010).*
(Continued)

*Primary Examiner* — Donald R Spamer
*Assistant Examiner* — Jeffrey D Benson
(74) *Attorney, Agent, or Firm* — Renner, Otto, Boisselle & Sklar, LLP (57) ABSTRACT

Disclosed herein are a microorganism growth inhibitor including allulose-containing saccharides and a fermented alcoholic beverage comprising the same.

6 Claims, 5 Drawing Sheets

(51) Int. Cl.
*C12N 1/16* (2006.01)
*C12N 1/20* (2006.01)

(58) Field of Classification Search
CPC .... C12G 2200/05; C12G 1/0203; C12H 1/14; A01N 43/08
See application file for complete search history.

(56) References Cited

U.S. PATENT DOCUMENTS

| | | | |
|---|---|---|---|
| 2008/0182752 | A1 | 7/2008 | Izumori et al. |
| 2012/0070534 | A1 | 3/2012 | Suzuki |
| 2014/0271746 | A1 | 9/2014 | Woodyer |
| 2014/0272068 | A1 | 9/2014 | Prakash |
| 2014/0373582 | A1 | 12/2014 | Mitarai et al. |
| 2016/0021917 | A1 | 1/2016 | Woodyer |
| 2016/0302463 | A1 | 10/2016 | Woodyer et al. |
| 2017/0027206 | A1 | 2/2017 | Woodyer |
| 2018/0289051 | A1* | 10/2018 | Higiro .................. A23L 27/36 |

FOREIGN PATENT DOCUMENTS

| | | |
|---|---|---|
| CN | 102399654 A | 4/2012 |
| CN | 103805552 B | 3/2016 |
| CN | 104371937 B | 7/2017 |
| CN | 105802897 B | 2/2019 |
| CN | 105338833 B | 6/2020 |
| CN | 105188421 B | 6/2021 |
| JP | 2001-252039 A | 9/2001 |
| JP | 2006-008669 A | 1/2006 |
| JP | 2010-119335 A | 5/2010 |
| JP | 2012-060930 A | 3/2012 |
| JP | 2014-014276 A | 1/2014 |
| JP | 5764308 | 8/2015 |
| KR | 2011-0085550 A | 7/2011 |
| KR | 10-2012-0029365 A | 3/2012 |
| KR | 10-1252810 B | 4/2013 |
| KR | 10-1352025 | 1/2014 |
| KR | 10-2016-0051084 A | 5/2016 |
| WO | WO-2015110484 A2 * 7/2015 ........... C12G 1/0203 |
| WO | 2016-065698 A1 | 5/2016 |

OTHER PUBLICATIONS

Wine with rare sugar! New release of red wine and white wine for Sanuki! @Ogush, Sep. 5, 2014, http://sanuki-asobinin.seesaa.net/article/405765771.html.

[Don't eat only looking ahead] What is the healthy 'sweetness' to replace sugar?, Apr. 10, 2015, http://www.consumuch.com/news/articleView.html?idxno=17789.

Hiroyuki Sasahara et al., "Effect of Rare Sugars on Growth of Intestinal Bacteria", Report of the Food Research Institute and the Fermentation & Food Experimental Station,Kagawa Prefectual Government, 2000, vol. 92, p. 7-8.

Oshima Hisaka et al., "Establishment of a high-sensitivity analysis method for rare sugars included in foods", Research Report, 2013, vol. 13, p. 100-102.

Extended European Search Report for corresponding European Patent Application No. 17858684.8 dated May 6, 2020.

Office Action dated Aug. 28, 2020, for related Canadian National Phase Patent Application No. 3,033,056.

W. Zhang et al., "Recent advances in D-allulose: Physiological functionalities, applications, and biological production", Trends in Food Science & Technology, 2016, vol. 54, pp. 127-137.

Office Action issued for corresponding Chinese National Stage application No. 202211012604.9, dated Mar. 18, 2023.

* cited by examiner

BACTERIAL, FUNGAL, AND YEAST GROWTH INHIBITOR CONTAINING ALLULOSE

FIELD OF THE INVENTION

The present invention relates to a growth inhibitor for bacteria, fungi, and yeasts that comprise allulose-containing saccharides.

DESCRIPTION OF THE RELATED ART

Fermented foods are rich in living microorganisms and continuously undergo fermentation. As time goes by, the number of microorganisms in fermented foods has changed dramatically, causing quality change such as changes in alcohol content or taste. Thus, distribution and sales for the fermented foods were limited.

Particularly, raw makgeolli, which is a fermented beverage, has a very short shelf of 7 to 10 days, and then it is substantially hard to keep long sales. In addition, wine, a fermented alcoholic beverage, is not kept constant in quality due to post-fermentation and thus requires a sterilization process or facilities for low temperature storage to prevent such quality change, from causing deterioration in sensory properties or cost increases The present inventors have made efforts to inhibit post-fermentation of the fermented alcoholic beverages. As a result, the present inventors found that addition of allulose can inhibit the growth of fungi (e.g., *Aspergillus oryzae*, *Asp. awamori*, *Monascus purpureus*, *Monascus ruber*, and *Rhizopus oryzae*), bacteria (e.g., *Lactobacillus casei* and *Lactococcus lactis* subsp. *lactis*), and yeasts (e.g., *Saccharomyces cerevisiae*) used for fermentation of makgeolli and the growth of yeasts (e.g., *Saccharomyces cerevisiae* and *Saccharomyces pastorianus*) used for fermentation of wine, thereby inhibit post-fermentation of fermented foods (e.g., fermented alcoholic beverages such as makgeolli and wine), and thus completed the present invention.

RELATED LITERATURE

Patent Document

Korean Patent No. 10-1352025

DISCLOSURE OF THE INVENTION

Technical Problem

It is one object of the present invention to provide a growth inhibitor for a microorganism, which includes allulose-containing saccharides.

It is another object of the present application to provide a fermented alcoholic beverage including the growth inhibitor.

It is a further object of the present application to provide a method for inhibiting post-fermentation of a fermented alcoholic beverage, which includes adding the growth inhibitor to the fermented alcoholic beverage.

Technical Solution

In accordance with one aspect of the present invention, a growth inhibitor for a microorganism includes allulose-containing saccharides, wherein the microorganism includes at least one selected from the group consisting of the following bacteria, fungi, and yeasts:

(i) *Lactobacillus casei* and *Lactococcus lactis* subsp. *lactis* as bacteria;
(ii) *Aspergillus oryzae*, *Aspergillus awamori*, *Monascus purpureus*, *Monascus ruber*, and *Rhizopus oryzae* as fungi; and
(iii) *Saccharomyces cerevisiae* and *Saccharomyces pastorianus* as yeasts.

The allulose used herein may be extracted directly from natural products, or may be chemically or biologically synthesized, without being limited thereto. In addition, the allulose may be provided in crystal form or in allulose-containing syrup form (i.e., in liquid form).

The allulose may be present in an amount of 50 parts by weight to 100 parts by weight relative to 100 parts by weight of the saccharides in terms of dried solid (DS) content. Specifically, the allulose may be present in an amount of 70 parts by weight to 100 parts by weight, 90 parts by weight to 100 parts by weight, 95 parts by weight to 100 parts by weight, 98 parts by weight to 100 parts by weight, 98.5 parts by weight to 100 parts by weight, 99 parts by weight to 100 parts by weight, or 99.5 parts by weight to 100 parts by weight, relative to 100 parts by weight of the saccharides in terms of dried solid content.

The saccharides may further include at least one sweetener, in addition to allulose. Examples of the sweetener may include any known sweetener (for example, monosaccharides, disaccharides, oligosaccharides, sugar alcohols, and high-strength sweeteners), without being limited thereto. Examples of the monosaccharides may include arabinose, xylose, fructose, tagatose, allose, and galactose. The disaccharides refer to a group of carbohydrates consisting of two monosaccharide units linked together, and examples thereof may include lactose, maltose, trehalose, turanose, and cellobiose. The oligosaccharides refer to a group of carbohydrates consisting of 3 or more monosaccharide units linked together, and examples thereof may include fructooligosaccharide, isomaltooligosaccharide, xylooligosaccharide, gentio-oligosaccharide, maltooligosaccharide, and galactooligosaccharide. The sugar alcohols refer to compounds obtained by reducing a carbonyl group in saccharides, and examples thereof may include erythritol, xylitol, arabitol, mannitol, sorbitol, maltitol, and lactitol. The high-strength sweeteners refer to sweeteners having a sweetness ten times or greater that of sucrose, and examples thereof may include aspartame, acesulfame K, rebaudioside A, and sucralose, without being limited thereto. In another embodiment, the saccharides according to the present invention may be free from sucrose, glucose, or a combination thereof.

The growth inhibitor may inhibit the growth of *Lactobacillus casei* or *Lactococcus lactis* subsp. *lactis* such that the number of single cell colonies measured after cultivation in MRS medium at 37° C. for 12, 24, or 48 hours is 300% or less, 200% or less, 180% or less, 150% or less, 130% or less, 120% or less, or 100% or less of the initial number of single cell colonies cultivated for 0 hour.

The growth inhibitor may inhibit the growth of *Aspergillus oryzae*, *Aspergillus awamori*, *Monascus purpureus*, *Monascus ruber*, or *Rhizopus oryzae* such that the number of single cell colonies measured after cultivation in PD medium at 25° C. for 24, 48, or 72 hours is 3,500% or less, 2,000% or less, 500% or less, 400% or less, 300% or less, 200% or less, 180% or less, 150% or less, 130% or less, 120% or less, 110% or less, or 100% or less of the initial number of single cell colonies cultivated for 0 hour.

The growth inhibitor may inhibit the growth of *Saccharomyces cerevisiae* or *Saccharomyces pastorianus* such that the number of single cell colonies measured after cultivation in YM medium at 25° C. for 24, 48, or 72 hours is 400% or less, 350% or less, 300% or less, 200% or less, 150% or less, 130% or less, 120% or less, 110% or less, or 100% or less of the initial number of single cell colonies cultivated for 0 hour.

In accordance with another aspect of the present invention, a fermented alcoholic beverage includes the growth inhibitor according to the present invention.

The fermented alcoholic beverage may include any known fermented alcoholic beverage obtained by inoculating an alcohol-producing microorganism into a fruit or cereal, followed by fermenting under specific conditions. Specifically, the fermented alcoholic beverage according to the present invention may be makgeolli, dongdongju, takju, wine, or beer, more specifically makgeolli or wine.

The fermented alcoholic beverage may be an alcoholic beverage fermented by at least one microorganism selected from the group consisting of the following bacteria, fungi, and yeasts: (i) *Lactobacillus casei* and *Lactococcus lactis* subsp. *lactis* as bacteria; (ii) *Aspergillus oryzae, Aspergillus awamori, Monascus purpureus, Monascus ruber*, and *Rhizopus oryzae* as fungi; and (iii) *Saccharomyces cerevisiae* and *Saccharomyces pastorianus* as yeasts.

The fermented alcoholic beverage may be a fermented alcoholic beverage including at least one microorganism selected from the group consisting of the following bacteria, fungi, and yeasts: (i) *Lactobacillus casei* and *Lactococcus lactis* subsp. *lactis* as bacteria; (ii) *Aspergillus oryzae, Aspergillus awamori, Monascus purpureus, Monascus ruber*, and *Rhizopus oryzae* as fungi; and (iii) *Saccharomyces cerevisiae* and *Saccharomyces pastorianus* as yeasts.

The fermented alcoholic beverage may further include food ingredients commonly used in a fermented alcoholic beverage. Specifically, the fermented alcoholic beverage according to the present invention may further include at least one food ingredient selected from the group consisting of purified water, oligosaccharide, rice, starch (e.g. maltodextrin), carbon dioxide gas, aspartame, an organic acid (e.g. citric acid) and a plant extract.

In the fermented alcoholic beverage, the growth inhibitor, the allulose, the saccharides, the bacteria, the fungi, and the yeasts are the same as described above.

In accordance with a further aspect of the present invention, a method for inhibiting post-fermentation of a fermented alcoholic beverage includes adding the growth inhibitor according to the present invention to the fermented alcoholic beverage.

Now, embodiments of the present invention will be described in more detail through a method of preparing a fermented alcoholic beverage. Examples of the fermented alcoholic beverage include representative makgeolli and wine as above. First, the embodiments of the present invention will be described in more detail through a method of preparing makgeolli including the following steps:

(1) preparing a mother liquor by fermenting an uncooked or cooked starch material using bacteria, yeasts or fungi;

(2) mashing the mother liquor prepared in step (1) by adding a starch material, a saccharifying agent, and water;

(3) fermenting the mashed product obtained in step (2), followed by aging;

(4) removing undissolved starch solids by sieving the aged product obtained in step (3); and (5) preparing a final product by adding allulose, saccharides, and water to the sieved product obtained in step (4).

As in the above method of preparing makgeolli, since a method for inhibiting post-fermentation of a fermented alcoholic beverage other than makgeolli, such as wine, according to the present invention is substantially the same as a typical wine production method except that the saccharides and allulose according to the present invention are added instead of typical saccharides or sweeteners, description thereof will be omitted.

In the method for inhibiting post-fermentation of a fermented alcoholic beverage, the growth inhibitor, the allulose, the saccharides, the bacteria, the fungi, and the yeasts are the same as described above.

Advantageous Effects

According to the present invention, it is possible to inhibit growth of microorganisms in a fermented alcoholic beverage, thereby to inhibit post-fermentation of the fermented alcoholic beverage. Specifically, when allulose is used instead of saccharides, such as sucrose, commonly added to fermented alcoholic beverages such as makgeolli or wine, the present invention can obtain the effects to prevent unintentional quality deterioration that can occur during storage or distribution of fermented alcoholic beverages and to eliminate a need for a separate process or device for improving storage stability, thereby to simplify the manufacturing process while reducing manufacturing costs.

DETAILED DESCRIPTION OF THE INVENTION

Hereinafter, the present invention will be described in more detail with reference to examples. However, it should be noted that these examples are provided for illustration only and should not be construed in any way as limiting the invention. In addition, these examples are provided for more complete understanding of the present invention by one of ordinary skill in the art.

EXAMPLES

Experimental Example 1: Preparation of Microorganism and Medium for Fermentation of Fermented Alcoholic Beverage In order to evaluate inhibition of post-fermentation of fermented alcoholic beverages, a degree of inhibition of the growth of microorganisms commonly used in fermented alcoholic beverages was determined.

Specifically, each of the microorganisms (bacteria, fungi, and yeasts) obtained from Korean Culture Center of Microorganisms (KCCM) was subcultured three or four times in a culture medium (Table 1) by a typical method to enhance activity. Then, the cultured microorganism was inoculated into a culture medium (Table 1), followed by inducing over-cultivation to a concentration of $10^5$ CFU/mL or more, thereby obtaining a strain mother liquor (Table 1).

Table 1

| Item | Name | KCCM | ATCC | Culture medium |
|---|---|---|---|---|
| Bacterium | Lactobacillus casei | 12452 | 393 | LACTOBACILI MRS (MRS) |
|  | Lactococcus lactis subsp. lactis | 41573 | 15577 | LACTOBACILI MRS (MRS) |
| Fungus | Aspergillus oryzae | 12698 | 1011 | POTATO DEXTROSE BROTH (PDB) |
|  | Aspergillus awamori | 60247 | 14331 | POTATO DEXTROSE BROTH (PDB) |
|  | Monascus purpureus | 35473 | 16365 | POTATO DEXTROSE BROTH (PDB) |
|  | Monascus ruber | 11845 | 16378 | POTATO DEXTROSE BROTH (PDB) |
|  | Rhizopus oryzae | 11697 | 4858 | POTATO DEXTROSE BROTH (PDB) |
| Yeast | Saccharomyces cerevisiae | 11304 | 9080 | YEAST MOLD BROTH (YMB) |
|  | Saccharomyces pastorianus | 11523 | 2345 | YEAST MOLD BROTH (YMB) |

Experimental Example 2: Confirmation for Growth of Microorganism Depending on Composition of Saccharides In order to compare degrees of inhibition of the growth of microorganisms depending upon the kind of purely added saccharides without a bias due to alcohol and other additives contained in a fermented alcoholic beverage, only the kind of saccharides added to a culture medium for each of the microorganisms was varied and investigated.

Specifically, as saccharides of a culture medium suited to each strain, water-containing crystalline glucose (purity 98 wt % or more, CJ Cheiljedang), sucrose (purity 98 wt % or more, CJ Cheiljedang), and crystalline allulose (purity: 98 wt % or more, CJ Cheiljedang) were added to each of the culture medium, thereby preparing a modified culture medium (Tables 2 to 4). Then, 100 mL of the prepared modified culture medium was inoculated with 1 mL of the mother liquor of each strain prepared in Experimental Example 1, followed by observation of time-dependent changes in cell number of each strain. That is, MRS media as listed in Table 2, PDB media as listed in Table 3, and YMB media as listed in Table 4 were inoculated with bacteria (*Lactobacillus casei* and *Lactococcus lactis* subsp. *lactis*), fungi (*Aspergillus oryzae, Aspergillus awamori, Monascus purpureus, Monascus ruber,* and *Rhizopus oryzae*), and yeasts (*Saccharomyces cerevisiae* and *Saccharomyces pastorianus*), respectively, in the same manner. Then, each of the media inoculated with the bacteria was stored at 37° C. for 12, 24 and 48 hours to be used as a specimen for measurement of the number of single cell colonies, and each of the media inoculated with the fungi or yeasts was stored at 25° C. for 24, 48, and 72 hours to be used as a specimen for measurement of the number of single cell colonies.

Measurement of the number of single cell colonies was carried out by a typical microorganism test. Specifically, 1 mL of each specimen was gradually diluted with 9 mL of 0.9% sterilized physiological saline by a 10-fold dilution method, thereby obtaining a diluted specimen. Thereafter, 1 mL of the diluted specimen was placed in a petri dish and 25 mL of a normal culture medium with agar added thereto was poured into the petri dish so as to be sufficiently mixed and solidified, thereby obtaining an inoculated specimen. Here, as the normal culture medium with agar added thereto, MRSA, PDA, and YMA were used for the bacteria, the fungi, and the yeasts, respectively.

Thereafter, the measured number of cell colonies was multiplied by a dilution factor, thereby calculating a value of colony forming unit (CFU) per mL of sample.

TABLE 2

| | Bacterium | |
|---|---|---|
| Comparative Example 1-1 | Comparative Example 1-2 | Example 1 |
| Protease peptone, 10.0 g | Protease peptone, 10.0 g | Protease peptone, 10.0 g |
| Beef extract, 8.0 g | Beef extract, 8.0 g | Beef extract, 8.0 g |
| Yeast extract, 4.0 g | Yeast extract, 4.0 g | Yeast extract, 4.0 g |
| Polysorbate (Tween 80), 1.0 g | Polysorbate (Tween 80), 1.0 g | Polysorbate (Tween 80), 1.0 g |
| Ammonium citrate, 2.0 g | Ammonium citrate, 2.0 g | Ammonium citrate, 2.0 g |
| Sodium acetate, 5.0 g | Sodium acetate, 5.0 g | Sodium acetate, 5.0 g |
| $K_2HPO_4$, 2.0 g | $K_2HPO_4$, 2.0 g | $K_2HPO_4$, 2.0 g |
| $MgSO_4 * 7H_2O$, 0.1 g | $MgSO_4 * 7H_2O$, 0.1 g | $MgSO_4 * 7H_2O$, 0.1 g |
| $MnSO_4 * 4H_2O$, 0.05 g | $MnSO_4 * 4H_2O$, 0.05 g | $MnSO_4 * 4H_2O$, 0.05 g |
| Distilled water, balance of 1.0 L | Distilled water, balance of 1.0 L | Distilled water, balance of 1.0 L |
| Glucose, 20.0 g | Sucrose, 20.0 g | Allulose, 20.0 g |

TABLE 3

| | Fungus | |
|---|---|---|
| Comparative Example 2-1 | Comparative Example 2-2 | Example 2 |
| POTATO STARCH, 4.0 g | POTATO STARCH, 4.0 g | POTATO STARCH, 4.0 g |
| Distilled water, balance of 1.0 L | Distilled water, balance of 1.0 L | Distilled water, balance of 1.0 L |
| Glucose, 20.0 g | Sucrose, 20.0 g | Allulose, 20.0 g |

TABLE 4

| | Yeast | |
|---|---|---|
| Comparative Example 3-1 | Comparative Example 3-2 | Example 3 |
| Yeast extract, 3.0 g | Yeast extract, 3.0 g | Yeast extract, 3.0 g |
| Malt extract, 3.0 g | Malt extract, 3.0 g | Malt extract, 3.0 g |
| Peptone, 5.0 g | Peptone, 5.0 g | Peptone, 5.0 g |
| Distilled water, balance of 1.0 L | Distilled water, balance of 1.0 L | Distilled water, balance of 1.0 L |
| Glucose, 10.0 g | Sucrose, 10.0 g | Allulose, 10.0 g |

As a result, it was confirmed that the number of cell colonies of the nine strains of Examples 1 to 3 using allulose as saccharides was significantly lower than that of the strains of Comparative Examples. In addition, it was confirmed that the strains of Comparative Examples 1-1, 2-1, and 3-1 using glucose as saccharides as in a typical culture medium exhibited a high degree of growth of microorganisms and the strains of Comparative Examples 1-2, 2-2, and 3-2 using sucrose as saccharides exhibited a degree of growth of microorganisms not significantly different from that of the strains inoculated using glucose as saccharides.

Figure 1:
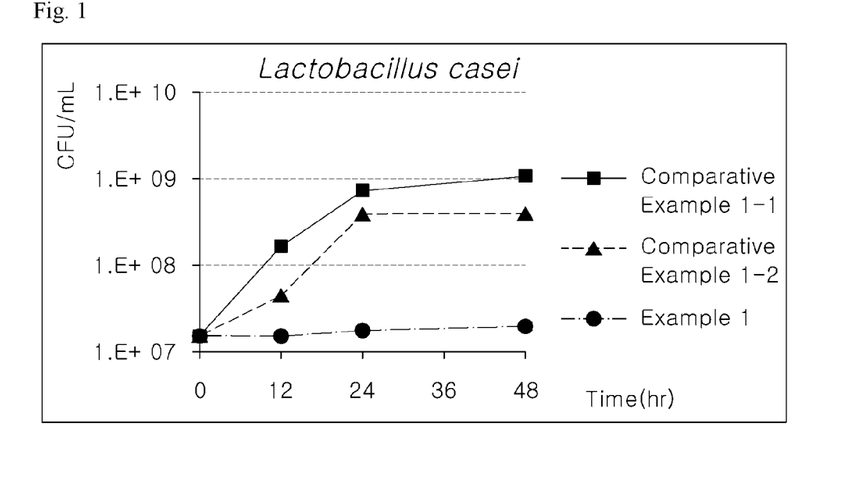
FIGS. 1 and 2 are graphs showing time-dependent CFU values for bacterial targets (*Lactobacillus casei* (FIG. 1) and *Lactococcus lactis* subsp. *lactis* (FIG. 2)), as measured on samples of Comparative Examples using glucose or sucrose as saccharides and samples of Examples using allulose as saccharides.
Figure 2:
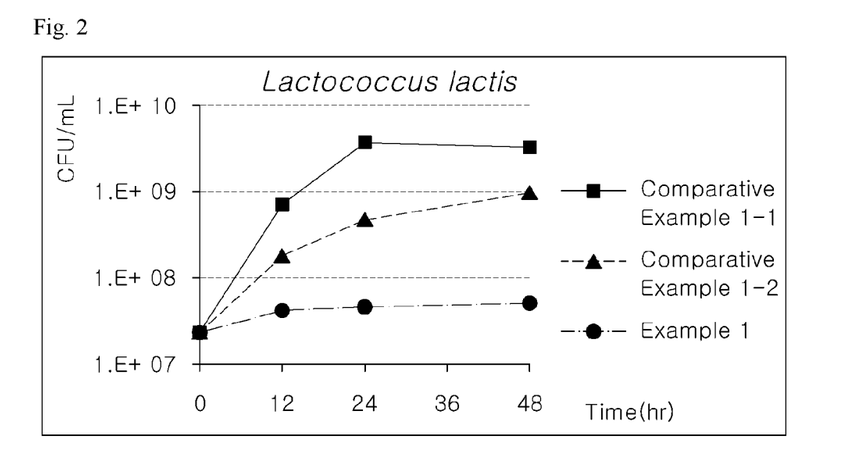
Figure 3:
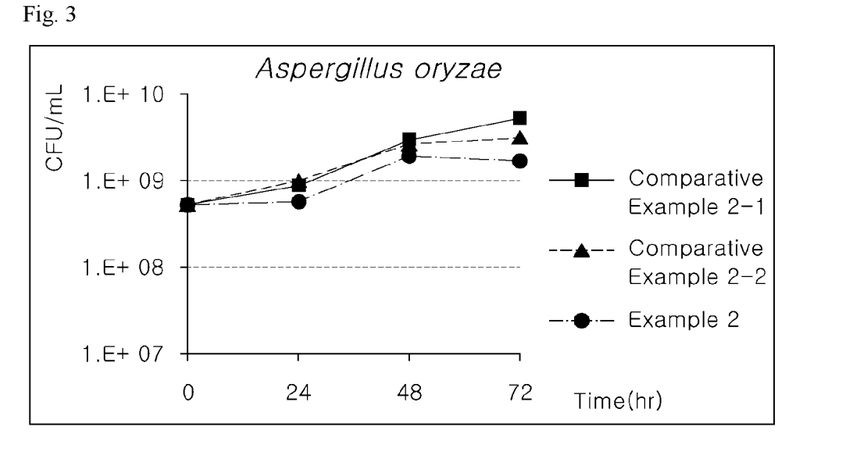
FIGS. 3 to 7 are graphs showing time-dependent CFU values for fungus targets (*Aspergillus oryzae* (FIG. 3), *Aspergillus awamori* (FIG. 4), *Monascus purpureus* (FIG. 5), *Monascus ruber* (FIG. 6), and *Rhizopus oryzae* (FIG. 7)), as measured on samples of Comparative Examples using glucose or sucrose as saccharides and samples of Examples using allulose as saccharides.
Figure 4:
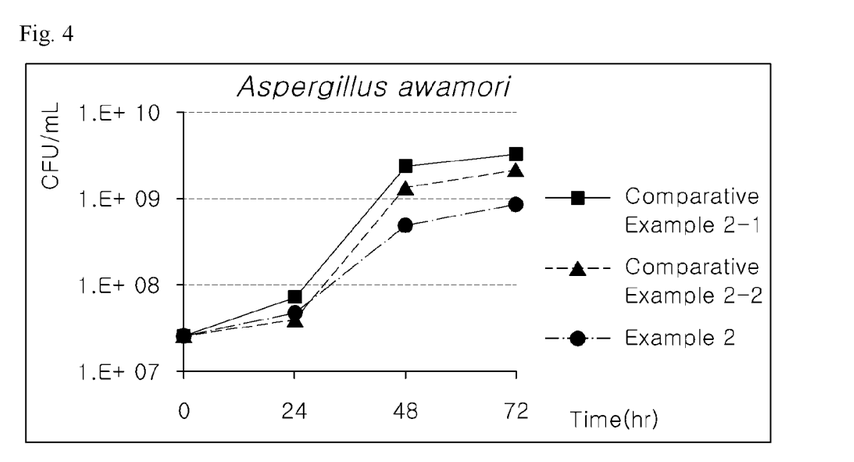
Figure 5:
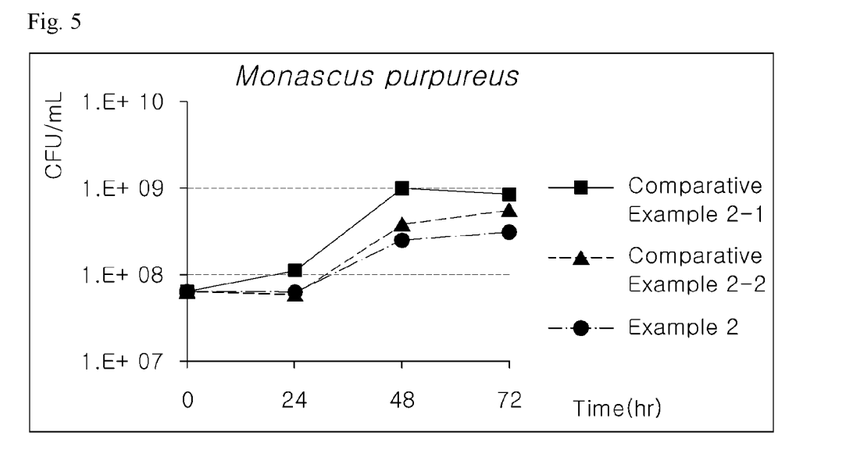
Figure 6:
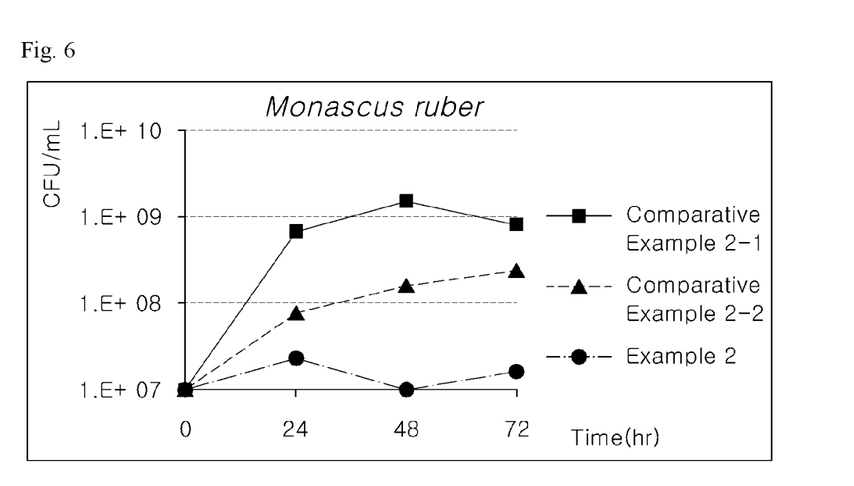
Figure 7:
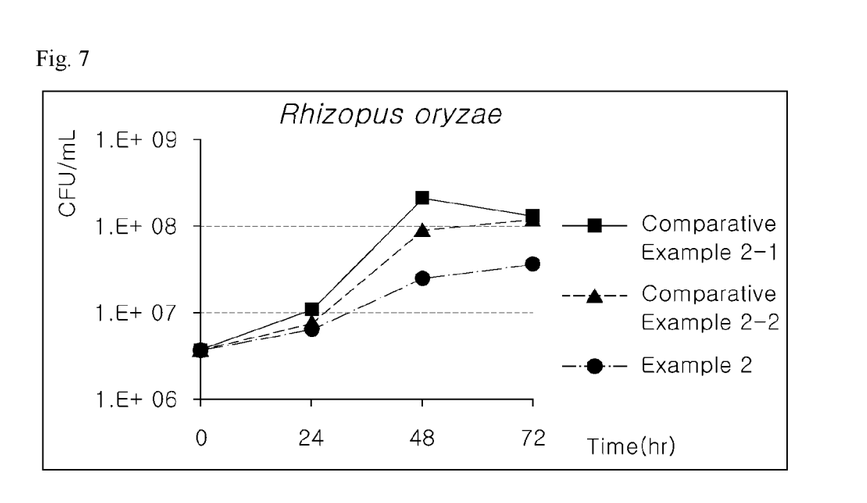

Specifically, *Lactobacillus casei* and *Lactococcus lactis* subsp. *lactis*, as bacteria, in a culture medium using glucose as saccharides (Comparative Example 1-1) and a culture medium using sucrose as saccharides (Comparative Example 1-2) were increased in cell number by 40.6 to 137 times. Conversely, the bacteria in a culture medium using allulose as saccharides were increased in cell number only by 1.3 to 2.2 times. Therefore, substantially no strain growth was observed (FIGS. 1 and 2).

In addition, *Aspergillus oryzae, Aspergillus awamori, Monascus purpureus, Monascus ruber* and *Rhizopus oryzae*, as fungi, were increased in cell number by 9.8 to 148.5 times in a culture medium using glucose as saccharides (Comparative Example 2-1) and 5.9 to 81.1 times in a culture medium using sucrose as saccharides (Comparative Example 2-2), respectively. Conversely, the fungi were increased in cell number only by 1.6 to 9.8 times in a culture medium using allulose as saccharides (Example 2). Therefore, statistically significant inhibition of microorganism growth was observed (FIGS. 3 to 7).

Figure 8:
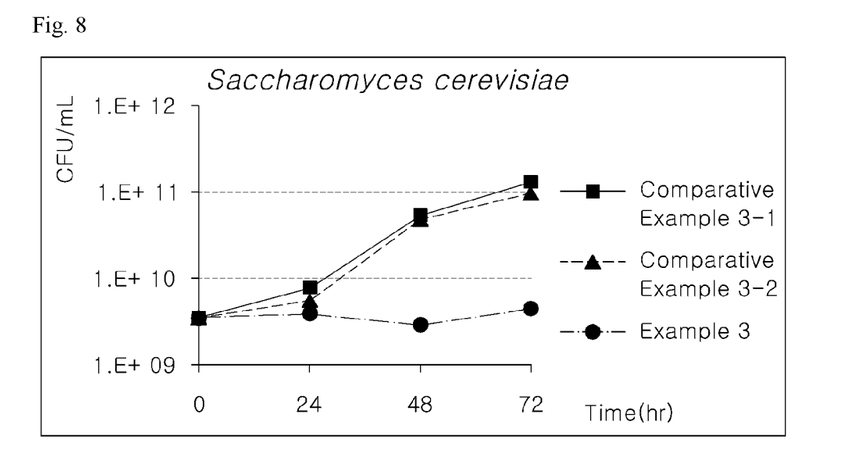
FIGS. 8 and 9 are graphs showing time-dependent CFU values for yeast targets (*Saccharomyces cerevisiae* (FIG. 8) and *Saccharomyces pastorianus* (FIG. 9)), as measured on samples of Comparative Examples using glucose or sucrose as saccharides and samples of Examples using allulose as saccharides.
Figure 9:
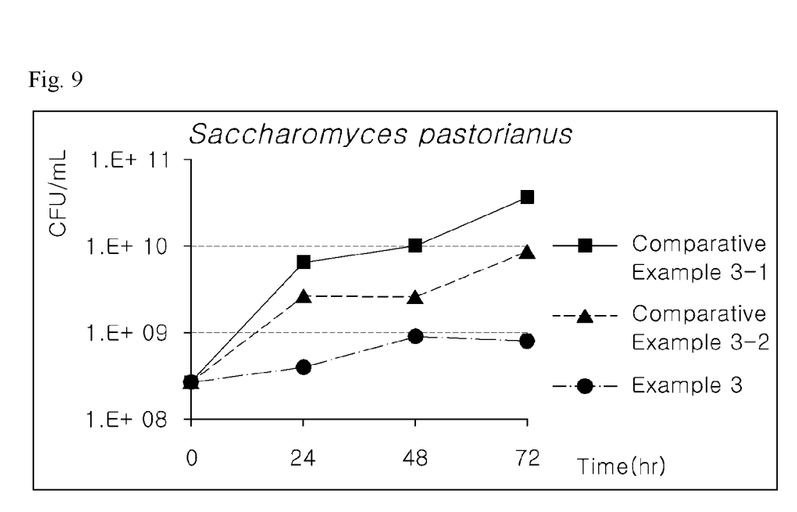

Finally, *Saccharomyces cerevisiae* and *Saccharomyces pastorianus*, as yeasts, in a culture medium using glucose as saccharides (Comparative Example 3-1) and a culture medium using sucrose as saccharides (Comparative Example 3-2) were increased in cell number by 27.4 to 134.8 times. Conversely, the yeasts in a culture medium using allulose as saccharides were increased in cell number only by 1.3 to 3 times. Therefore, substantially no strain growth was observed (FIGS. 8 and 9).

For each of the strains, the number of single colonies was measured after cultivation for 0, 12, 24, 48, and 72 hours in each of the culture media. Results are shown in Table 5.

TABLE 5

| Strain | Medium-dependent classification | 0 hours | 12 hours | 24 hours | 48 hours | Culture medium (saccharides) |
|---|---|---|---|---|---|---|
| *Lactobacillus casei* | Comparative Example 1-1 | $1.5 \times 10^7$ | $1.7 \times 10^8$ | $7.3 \times 10^8$ | $1.1 \times 10^9$ | MRS (glucose) |
| | Comparative Example 1-2 | $1.5 \times 10^7$ | $4.5 \times 10^7$ | $3.9 \times 10^8$ | $4.0 \times 10^8$ | MRS (sucrose) |
| | Example 1 | $1.5 \times 10^7$ | $1.5 \times 10^7$ | $1.8 \times 10^7$ | $2.0 \times 10^7$ | MRS (allulose) |
| *Lactococcus lactis* subsp. *lactis* | Comparative Example 1-1 | $2.4 \times 10^7$ | $7.0 \times 10^8$ | $3.6 \times 10^9$ | $3.3 \times 10^9$ | MRS (glucose) |
| | Comparative Example 1-2 | $2.4 \times 10^7$ | $1.8 \times 10^8$ | $4.8 \times 10^8$ | $9.7 \times 10^8$ | MRS (sucrose) |
| | Example 1 | $2.4 \times 10^7$ | $4.2 \times 10^7$ | $4.6 \times 10^7$ | $5.2 \times 10^7$ | MRS (allulose) |

| Strain | Medium-dependent classification | 0 hours | 24 hours | 48 hours | 72 hours | culture medium |
|---|---|---|---|---|---|---|
| *Aspergillus oryzae* | Comparative Example 2-1 | $5.3 \times 10^8$ | $8.7 \times 10^8$ | $3.0 \times 10^9$ | $5.2 \times 10^9$ | PDB (glucose) |
| | Comparative Example 2-2 | $5.3 \times 10^8$ | $1.0 \times 10^9$ | $2.7 \times 10^9$ | $3.1 \times 10^9$ | PDB (sucrose) |
| | Example 2 | $5.3 \times 10^8$ | $5.7 \times 10^8$ | $1.9 \times 10^9$ | $1.7 \times 10^9$ | PDB (allulose) |
| *Aspergillus awamori* | Comparative Example 2-1 | $2.6 \times 10^7$ | $7.2 \times 10^7$ | $2.4 \times 10^9$ | $3.3 \times 10^9$ | PDB (glucose) |
| | Comparative Example 2-2 | $2.6 \times 10^7$ | $4.0 \times 10^7$ | $1.3 \times 10^9$ | $2.1 \times 10^9$ | PDB (sucrose) |
| | Example 2 | $2.6 \times 10^7$ | $4.8 \times 10^7$ | $4.9 \times 10^8$ | $8.6 \times 10^8$ | PDB (allulose) |
| *Monascus purpureus* | Comparative Example 2-1 | $6.4 \times 10^7$ | $1.1 \times 10^8$ | $9.9 \times 10^8$ | $8.6 \times 10^8$ | PDB (glucose) |
| | Comparative Example 2-2 | $6.4 \times 10^7$ | $5.9 \times 10^7$ | $3.8 \times 10^8$ | $5.6 \times 10^8$ | PDB (sucrose) |
| | Example 2 | $6.4 \times 10^7$ | $6.3 \times 10^7$ | $2.5 \times 10^8$ | $3.1 \times 10^8$ | PDB (allulose) |
| *Monascus ruber* | Comparative Example 2-1 | $1.0 \times 10^7$ | $6.8 \times 10^8$ | $1.5 \times 10^9$ | $8.0 \times 10^8$ | PDB (glucose) |
| | Comparative Example 2-2 | $1.0 \times 10^7$ | $7.7 \times 10^7$ | $1.6 \times 10^8$ | $2.4 \times 10^8$ | PDB (sucrose) |
| | Example 2 | $1.0 \times 10^7$ | $2.3 \times 10^7$ | $1.0 \times 10^7$ | $1.6 \times 10^7$ | PDB (allulose) |
| *Rhizopus oryzae* | Comparative Example 2-1 | $3.7 \times 10^6$ | $1.1 \times 10^7$ | $2.1 \times 10^8$ | $1.3 \times 10^8$ | PDB (glucose) |
| | Comparative Example 2-2 | $3.7 \times 10^6$ | $7.4 \times 10^6$ | $8.9 \times 10^7$ | $1.2 \times 10^8$ | PDB (sucrose) |
| | Example 2 | $3.7 \times 10^6$ | $6.4 \times 10^6$ | $2.5 \times 10^7$ | $3.6 \times 10^7$ | PDB (allulose) |
| *Saccharomyces cerevisiae* | Comparative Example 3-1 | $3.5 \times 10^9$ | $7.7 \times 10^9$ | $5.3 \times 10^{10}$ | $1.3 \times 10^{11}$ | YMB (glucose) |
| | Comparative Example 3-2 | $3.5 \times 10^9$ | $5.6 \times 10^9$ | $4.8 \times 10^{10}$ | $9.7 \times 10^{10}$ | YMB (sucrose) |

TABLE 5-continued

|  | | | | | | |
|---|---|---|---|---|---|---|
|  | Example 3 | $3.5 \times 10^9$ | $3.9 \times 10^9$ | $2.9 \times 10^9$ | $4.5 \times 10^9$ | YMB (allulose) |
| Saccharomyces pastorianus | Comparative Example 3-1 | $2.7 \times 10^8$ | $6.4 \times 10^9$ | $1.0 \times 10^{10}$ | $3.6 \times 10^{10}$ | YMB (glucose) |
|  | Comparative Example 3-2 | $2.7 \times 10^8$ | $2.6 \times 10^9$ | $2.6 \times 10^9$ | $8.6 \times 10^9$ | YMB (sucrose) |
|  | Example 3 | $2.7 \times 10^8$ | $4.0 \times 10^8$ | $8.9 \times 10^8$ | $8.0 \times 10^8$ | YMB (allulose) |

In conclusion, it can be seen that, when allulose is used instead of sucrose commonly used as a sweetener added to fermented alcoholic beverages such as makgeolli, it is possible to reduce post-fermentation caused by growth of microorganisms that can occur during production or distribution of the fermented alcoholic beverages.

Although some exemplary embodiments have been described herein, it should be understood by those skilled in the art that these embodiments are given by way of illustration only, and that various modifications, variations and alterations can be made without departing from the spirit and scope of the invention. Therefore, the embodiments and the accompanying drawings should not be construed as limiting the technical spirit of the present invention, but should be construed as illustrating the technical spirit of the present invention. The scope of the invention should be interpreted according to the following appended claims as covering all modifications or variations derived from the appended claims and equivalents thereof.

What is claimed is:

1. A fermented alcoholic beverage comprising:
   (a) at least one microorganism selected from the group consisting of *Lactobacillus casei* and *Lactococcus lactis* subsp. *lactis;* and
   (b) a growth inhibitor for a microorganism, comprising: allulose-containing saccharides; wherein the microorganism comprises at least one selected from the group consisting of *Lactobacillus casei* and *Lactococcus lactis* subsp. *lactis;*
   wherein the allulose is present in an amount of 50 parts by weight to 100 parts by weight relative to 100 parts by weight of the saccharides based on dried solid content.

2. The fermented alcoholic beverage according to claim 1, wherein the fermented alcoholic beverage is makgeolli or wine.

3. The fermented alcoholic beverage according to claim 1, wherein the fermented alcoholic beverage is fermented using at least one microorganism selected from the group consisting of *Lactobacillus casei* and *Lactococcus lactis* subsp. *lactis*.

4. The fermented alcoholic beverage of claim 1, wherein the saccharides are free from sucrose, glucose, or a combination thereof.

5. The fermented alcoholic beverage according to claim 4, wherein the fermented alcoholic beverage is makgeolli or wine.

6. The fermented alcoholic beverage according to claim 4, wherein the fermented alcoholic beverage is fermented using at least one microorganism selected from the group consisting of *Lactobacillus casei* and *Lactococcus lactis* subsp. *lactis*.

* * * * *